United States Patent

Roe et al.

[11] Patent Number: 5,989,236
[45] Date of Patent: Nov. 23, 1999

[54] ABSORBENT ARTICLE WITH ADJUSTABLE WAIST FEATURE

[75] Inventors: Donald C. Roe, West Chester; Kimberly A. Dreier; Constance Lee Fisher, both of Cincinnati; Carl L. Bergman, Loveland, all of Ohio

[73] Assignee: The Procter & Gamble Company, Cincinnati, Ohio

[21] Appl. No.: 09/042,421

[22] Filed: Mar. 13, 1998

Related U.S. Application Data

[60] Provisional application No. 60/049,511, Jun. 13, 1997.

[51] Int. Cl.⁶ ..................................................... A61F 13/15
[52] U.S. Cl. ........................................ 604/385.1; 604/391
[58] Field of Search ................................ 604/385.1, 386, 604/391, 389

[56] References Cited

U.S. PATENT DOCUMENTS

| | | | |
|---|---|---|---|
| 2,566,139 | 8/1951 | Ostrovsky et al. | 604/386 |
| 3,618,608 | 11/1971 | Brink | 604/391 |
| 4,728,326 | 3/1988 | Gilles | 604/391 |
| 5,106,385 | 4/1992 | Allen et al. | 604/391 |
| 5,112,356 | 5/1992 | Quedrini | 604/391 |
| 5,279,604 | 1/1994 | Robertson et al. | 604/391 |
| 5,318,555 | 6/1994 | Siebers et al. | 604/391 |

FOREIGN PATENT DOCUMENTS

| | | | |
|---|---|---|---|
| 0 627 210 A2 | 5/1994 | European Pat. Off. . | |
| 0 639 362 A2 | 8/1994 | European Pat. Off. . | |
| 5137754 | 6/1993 | Japan | 604/386 |
| 684050 | 7/1994 | Switzerland | 604/386 |
| WO 96/18367 | 6/1996 | WIPO . | |

*Primary Examiner*—Mark O. Polutta
*Attorney, Agent, or Firm*—David M. Weirich; Steven W. Miller; Jacobus C. Rasser

[57] ABSTRACT

A disposable absorbent article including a chassis having a body facing surface and a garment facing surface. The disposable absorbent article also includes a fold down waist feature disposed in the rear waist region which extends longitudinally outwardly from the rear waist edge of the core and includes at least one ear flap extending laterally outwardly from one of the longitudinal edges of the core. A fastening system for joining a portion of the front waist region and a portion of the rear waist region is provided. The fastening system preferably includes a first fastening element disposed on the inner surface of the side panel, a second fastening element disposed on the outer surface of the side panel and a third fastening element disposed on the garment facing surface of the chassis in the front waist region. Both the first fastening element and the second fastening element are separately engageable with the third fastening element such that the absorbent article may be fitted to a wearer in a first configuration wherein the first fastening element is engaged with the third fastening element and a second configuration wherein at least a portion of the waist feature is folded longitudinally inwardly.

4 Claims, 6 Drawing Sheets

ABSORBENT ARTICLE WITH ADJUSTABLE WAIST FEATURE

This application claims the benefit of U.S. Provisional Application Ser. No. 60/049,511 filed Jun. 13, 1997.

FIELD OF THE INVENTION

The present invention relates to disposable absorbent articles having length adjustable chasses and versatile fastening systems. Examples of such disposable articles include training pants, pull-on diapers or adult incontinence articles, disposable underwear and disposable panties which may be used with catamenial devices such as tampons or sanitary napkins.

BACKGROUND OF THE INVENTION

Infants and other incontinent individuals wear absorbent articles to receive and contain urine and other bodily exudates. Many consumers prefer disposable absorbent articles because of their convenience and often superior containment characteristics. However, because disposable articles are intended to be discarded, generally after a single use, consumers are very conscious of the cost of such articles. One way to reduce the cost of such articles is to manufacture a single article which performs well on a large range of wearer sizes and body shapes. This is especially important for newborn users because of their rapid growth rate. Another cost reduction feature may be to permit the absorbent article to be fitted to the wearer in more than one configuration such that the diaperer has a choice as to which features of the diaper will be used. Thus, it would be advantageous to provide a diaper that could be adjusted to fit a large range of wearer sizes. It would also be advantageous to provide a diaper which could be constructed in more than one configuration, as desired by the diaperer.

Therefore, it would be advantageous to provide a diaper which has a waist feature capable of adjusting the length of the diaper. It would also be advantageous to provide a diaper with a fold-down waist feature which permits the diaper to adjust in length to fit a large range of wearer sizes. Further, it would be desirable to provide a diaper which can be fitted to the wearer in more than one configuration. Also, it would be advantageous to provide an absorbent article which can be fitted to a wearer in a high-back configuration, or a low-back configuration. Finally, it would be desirable to provide a diaper with a fold-down back feature and a fastening system which permits the diaper to be adjusted in length.

SUMMARY OF THE INVENTION

The present invention relates to a disposable absorbent article including a chassis having a body facing surface and a garment facing surface. The chassis preferably comprises a topsheet forming at least a portion of the body facing surface of the chassis, a backsheet joined with the topsheet the backsheet forming at least a portion of the garment facing surface of the chassis, and a core disposed between the topsheet and the backsheet. The core has a front waist edge disposed in the front waist region, a rear waist edge disposed in the rear waist region and a pair of longitudinal edges. The disposable absorbent article preferably also includes a fold down waist feature disposed in the rear waist region which extends longitudinally outwardly from the rear waist edge of the core and includes at least one ear flap extending laterally outwardly from one of the longitudinal edges of the core. The ear flap has an inner surface and an opposed outer surface. A fastening system for joining a portion of the front waist region and a portion of the rear waist region is provided. The fastening system preferably includes a first fastening element disposed on the inner surface of the side panel, a second fastening element disposed on the outer surface of the side panel and a third fastening element disposed on the garment facing surface of the chassis in the front waist region. Both the first fastening element and the second fastening element are separately engageable with the third fastening element such that the absorbent article may be fitted to the wearer in a first configuration wherein the first fastening element is engaged with the third fastening element and a second configuration wherein at least a portion of the waist feature is folded longitudinally inwardly and the second fastening element is engaged with the third fastening element.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

The present invention generally relates to length adaptable disposable absorbent articles comprising versatile fastening systems. However, it should be noted that the article can be disposable and not an absorbent article as described herein, or can be reusable and thus, not disposable. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. As used herein, the term "diaper" refers to an absorbent article generally worn by infants and incontinent persons that is generally worn about the lower torso of the wearer. However, the present invention is also applicable to other absorbent articles such as incontinence briefs, diaper holders, feminine hygiene articles, training pants, panties, underwear and the like. One preferred embodiment of the present invention is the disposable absorbent article shown in FIG. 1.

Figure 1:
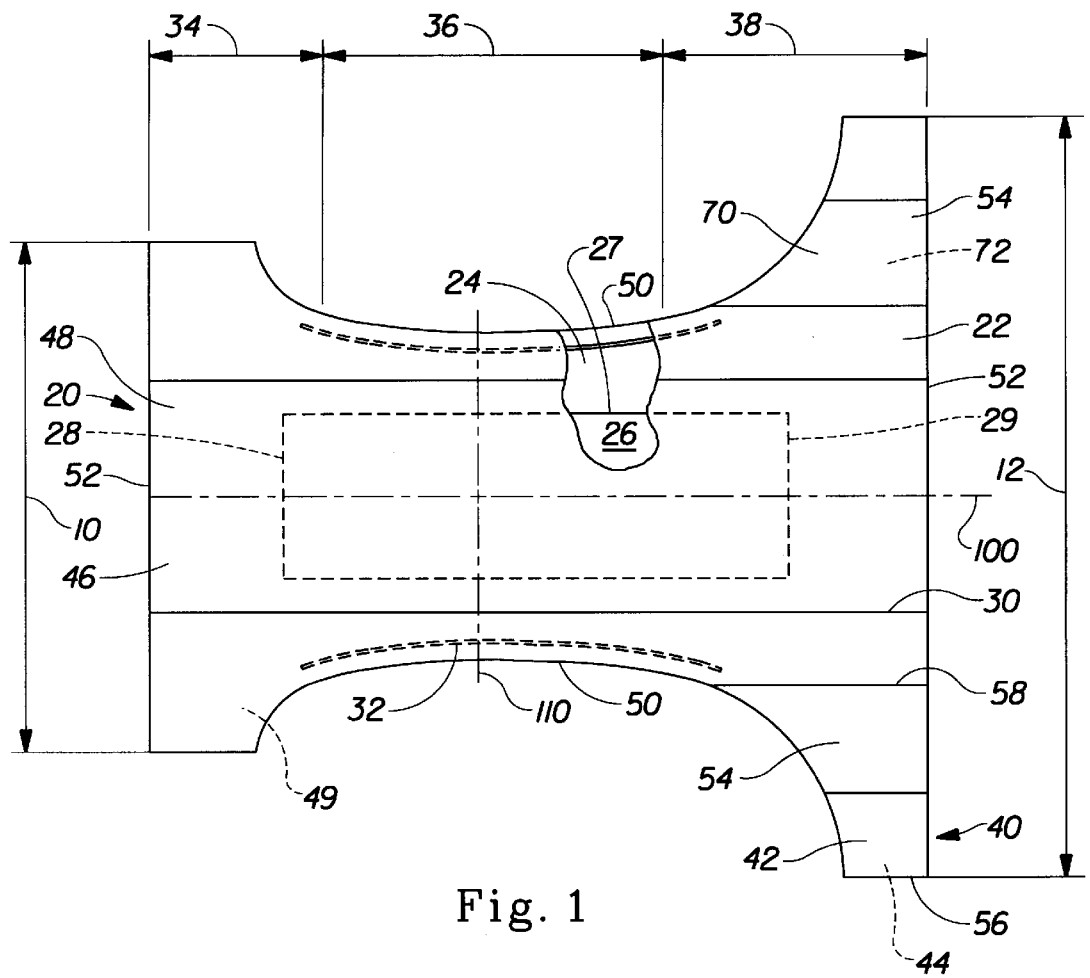
FIG. 1 is a plan view of a disposable absorbent article shown with the body facing side toward the viewer.
Figure 2:
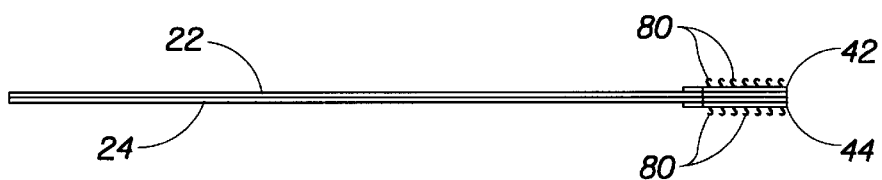
FIG. 2 is a side elevation of the absorbent article of FIG. 1.

With reference to FIG. 1, an absorbent article, such as diaper 20, generally comprises a chassis 46 having a pair of longitudinal edges 50, a liquid permeable topsheet 22, a liquid impermeable backsheet 24, and an absorbent core 26 between the topsheet 22 and the backsheet 24. The diaper 20 preferably further comprises a front waist region 34, a rear waist region 38, a crotch region 36 disposed between the front waist region 36 and the rear waist region 38, barrier leg cuffs 30 and/or gasketing cuffs 32, ear flaps 54, and a fastening system 40. (It should be understood that the front waist region 34 and the rear waist region 38 are defined as such merely as one preferred embodiment. However, embodiments are contemplated wherein what is herein described as the front waist region 34 could be the rear waist region 38, and vice versa.) The absorbent article has a first lateral dimension 10 in the front waist region 34 which is preferably less than the second lateral dimension 12 in the rear waist region. An example of a preferred absorbent article which may be modified to have the features of the present invention is more fully and completely described in U.S. Pat. No. 5,151,092 entitled "Absorbent Article With Dynamic Elastic Waist Feature Having a Predisposed Resilient Flexural Hinge", issued to Buell, et al. on Sep. 29, 1992 which is hereby incorporated by reference herein.

The absorbent core 26 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones. a hydrophilic gradient, a superabsorbent gradient, or lower average density and lower average basis weight acquisition zones; or may comprise one or more layers or structures). An exemplary absorbent structure for use as the absorbent core 26 of the present invention are described in U.S. Pat. No. 4,610,678 entitled "High-Density Absorbent Structures" issued to Weisman and Goldman on Sep. 9, 1986; U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989. Each of these references are incorporated herein by reference.

The backsheet 24 is positioned adjacent the garment-facing surface 1 of the absorbent core 24 and is preferably joined thereto by attachment means such as those well known in the art. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.) The backsheet 24 is preferably impervious to liquids (e.g. urine) and is preferably manufactured from a thin plastic film, or nonwoven material, although other flexible liquid impervious materials may also be used. As used herein, the term "flexible" refers to materials which are compliant and will readily conform to the general shape and contours of the human body. The backsheet 24 preferably prevents the exudates absorbed and contained in the absorbent core 26 from wetting articles which contact the diaper 20 such as bedsheets and undergarments. The backsheet 26 may comprise woven or nonwoven materials, polymeric films such as thermoplastic films of polyethylene or polypropylene, or composite materials such as a film-coated nonwoven material.

The topsheet 22 is preferably positioned adjacent the body-facing surface of the absorbent core 26 and is preferably joined thereto and to the backsheet 24 by attachment means such as those well known in the art. The topsheet 22 is preferably compliant, soft feeling, and nonirritating to the wearer's skin. Further, the topsheet 22 is liquid pervious, permitting liquids (e.g. urine) to readily penetrate through its thickness. A suitable topsheet 22 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. In one embodiment, the topsheet 22 is made of hydrophilic material comprising about 20% to 30% rayon so as to feel wet and signal a discharge of urine to a toilet training child. A suitable topsheet is manufactured by Fiberweb North America and available as 80/20 polypropylene/rayon carded thermally bonded nonwoven.

The topsheet 22, the backsheet 24, portions thereof or any other element of the diaper 20 may include "zero strain" stretch laminates. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the topsheet 22, backsheet 24, portions thereof or any other element of the disposable article 20 may comprise a structural elastic-like film (SELF) web. A structural elastic-like film web is an extensible material that exhibits an elastic-like behavior in the direction of elongation without the use of added elastic materials. SELF webs suitable for the present invention are more completely described in U.S. Pat. No. 5,554,145 entitled "Absorbent Article with Multiple Zone Structural Elastic-Like Film Web Extensible Waist Feature" issued to Donald C. Roe, et al. on Sep. 10, 1996, and U.S. Pat. No. 5,518,801 entitled "Web Materials Exhibiting Elastic-Like Behavior" issued to Chappell, et al. on May 21, 1996, both of which are incorporated herein by reference.

The disposable diaper 20 preferably further comprises leg cuffs 30 and 32 for providing improved containment of liquids and other body exudates. Each leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractible Side Portions For a Disposable Diaper" issued to Buell on Jan. 14, 1975, describes a disposable diaper which provides a contractible leg opening having a side flap and one or more elastic members to provide an elasticized leg cuff (gasketing cuff 32). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs 30) to improve the containment of the leg regions. While each leg cuff may be configured so as to be similar to any of the leg bands, side flaps, barrier cuffs, or elastic cuffs described above, it is preferred that each leg cuff comprise one or more elastic strands. U.S. Pat. No. 4,695,278 entitled "Absorbent Article Having Dual Cuffs" issued to Lawson on Sept. 22, 1987, describes a disposable diaper having dual cuffs including a gasketing cuff 32 and a barrier cuff 30. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference.

The disposable absorbent article of the present invention preferably also includes an ear flap 54 that extends laterally outwardly from at least one of the longitudinal edges 50 of the chassis 46, preferably in at least the rear waist region 38. As shown in FIG. 1, an ear flap 54 may extend outwardly from each of the longitudinal edges 50 of the chassis 46. The ear flap(s) 54 may be integral with any element or elements of the chassis 46 (i.e. extensions of the topsheet 22, the backsheet 24, or both), or may be a separate member joined to the chassis 46. Further, the ear flap(s) 54 may be single or multiple components which may include extensible or non-extensible materials. Elastically extensible ear flaps 54 help provide a more comfortable and contouring fit by initially conformably fitting the disposable garment to the wearer and sustaining the fit throughout the time of wear, well past when the disposable garment has been loaded with exudates because the ear flaps 54 allow the sides of the diaper 20 to expand and contract. In embodiments where the ear flaps 54 are separate members, it is preferred that at least a portion of the proximal edge 58 of each ear flap 54 be joined adjacent one of the opposing longitudinal edges 50 of the chassis 46. (The distal edge 56 of the ear flap 54 is disposed laterally outwardly from the proximal edge 58 when the diaper is in a flat-out, uncontracted state. In FIG. 1, the ear flaps 54 are shown to be integral members of the diaper 20, thus, the proximal edges 58 of the ear flaps 54 are shown by imaginary lines.) The ear flaps 54 may be joined by any means known in the art, including adhesives, heat, pressure, ultrasonics or any combination thereof. Further the ear flaps 54 may be disposed on the topsheet 22, the backsheet 24 or between the topsheet 22 and the backsheet 24, and may be joined to the topsheet 22, the backsheet 24 or both. Alternative embodiments of the present invention may also include ear flaps disposed in the front waist region 34.

Preferably, the disposable absorbent article 20 includes a fastening system 40. The fastening system 40 is designed to join at least a portion of the rear waist region 38 with the front waist region 34 to form a leg closure. If both sides of the diaper 20 are closed, a waist hoop and two leg closures are formed. As shown in FIG. 1, fastening elements 42, 44 are preferably disposed adjacent the distal edge 56 of the ear flap 54. In one configuration a first fastening element 42 is preferably disposed on the inner surface 70 of the ear flap 54 and the second fastening element 44 is disposed on the outer surface 72 of the ear flap 54. A third fastening element 45 is preferably disposed in the front waist region 34, preferably on the garment facing surface of the chassis 49. However, embodiments are contemplated wherein the third fastening element 45 is disposed on the body facing surface of the chassis 48.

In preferred embodiments, the first fastening element 42 and/or the second fastening element 44 each include an engaging member such as an adhesive or a hook of a hook and loop fastener. However, any other known fastening means can be used as the first and/or second fastening elements. Further, the first fastening element 42 may be the same as or different than the second fastening element 44 and either the first fastening element 42 or the second fastening element may include more than one type of fastening means. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987. Suitable mechanical fastening systems are described in U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; and U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents is hereby incorporated by reference herein. Other fastening systems may include cohesives, snaps, buttons, hook-and-eye fasteners, electrostatic fields, magnetic fields, and the like or any combination of these or other known fastening means.

The third fastening element 45 is preferably chosen such that it is engageable with both the first fastening element 42 and the second fastening element 44. Accordingly, if the first fastening element 42 and the second fastening element 44 are adhesives, the third fastening element 45 is preferably a release means such as a release strip or release surface. Suitable release means are described in further detail in U.S. Pat. No. 3,848,594 issued to Buell on Nov. 19, 1974; U.S. Pat. No. 4,662,875 issued to Hirotsu and Robertson on May 5, 1987, and U.S. Pat. No. 5,487,809 issued to Goulait et al. on Jan. 30, 1996. Alternatively, if the first fastening element 42 and the second fastening element 44 include hooks, or the like, the third fastening element 45 is preferably some type of loop or female component capable of engaging the first and second fastening elements. Suitable loop components are further described in U.S. Pat. No. 5,547,531 entitled "Nonwoven Female Component For Refastenable Fastening Device and Method of Making the Same" issued to Allen, et al. on Aug. 20, 1996; U.S. Pat. No. 5,595,567 entitled "Nonwoven Female Component For Refastenable Fastening Device" issued to King, et al. on Jan. 21, 1997; and U.S. Pat. No. 5,624,427 entitled "Female Component For Refastenable Fastening Device" issued to Bergman et al. on Apr. 29, 1997. Each of the above-mentioned patents is incorporated herein by reference.

Figure 3:
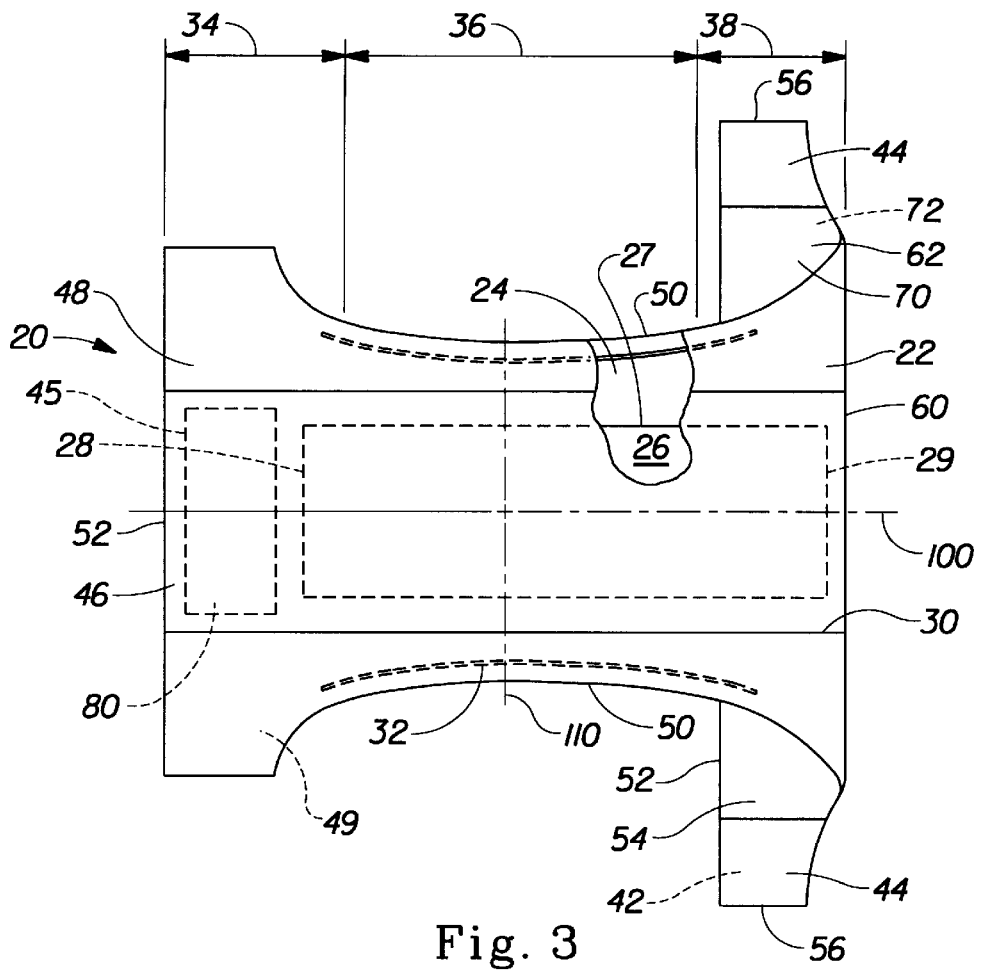
FIG. 3 a plan view of a disposable absorbent article shown in a folded configuration with the body facing side toward the viewer.
Figure 4:
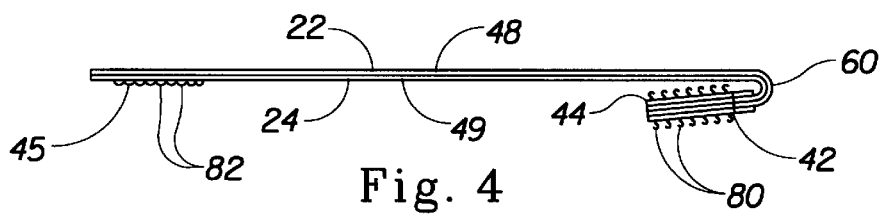
FIG. 4 is a side elevation of the absorbent article of FIG. 3.
Figure 5:
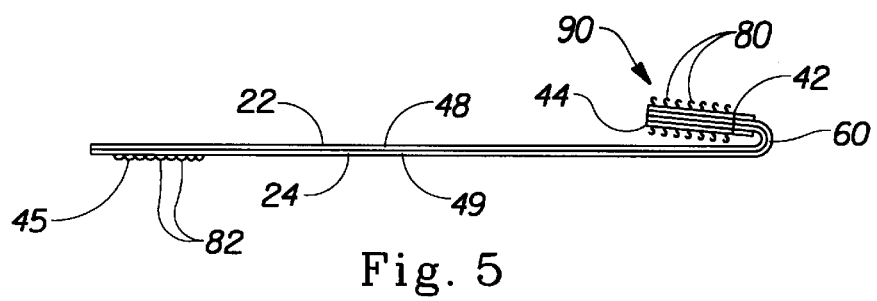
FIG. 5 is a side elevation of an alternative embodiment of the invention.

The ear flaps 54 and the fastening system 40 provide the disposable absorbent article of the present invention with a unique fold down waist feature 62. As shown in FIGS. 3–5, at least a portion of the rear waist region 38 of the diaper 20 may be folded longitudinally inwardly over either the garment facing surface 49 of the chassis 46 or the body facing surface 48 of the chassis 46. (As used herein, the term "longitudinally inwardly" means toward the lateral centerline 110 of the chassis 46.) Thus, the diaperer may fold all or any portion of the rear waist region 38 of the diaper 20 longitudinally inwardly to shorten the overall length of the diaper and to improve fit and containment characteristics. If the waist feature 62 is folded over the body facing surface 48 of the chassis, as shown in FIG. 5, it may provide the diaper 20 with a waist cap 90. The waist cap 90 may help prevent bodily exudates, especially feces, deposited in the diaper 20 from leaking out the rear waist region 38.

As shown in FIG. 3, all or a portion of the ear flap(s) 54 may be included in the fold down waist feature 62. Thus, the benefits of the ear flaps 54 are realized when the diaper 20 is fitted to the wearer in a traditional configuration (unfolded) or in any folded configuration. In a traditional configuration, the waist feature 62 is left fully longitudinally extended, as shown in FIG. 1. In such configurations, the first fastening elements 42 disposed on the inner surface 70 of ear flaps 54 are engageable with the third fastening element 45 disposed on the garment facing surface 49 of the chassis 46. In a folded configuration, where any or all of the waist feature 62 is folded longitudinally inwardly, the second fastening elements 44 disposed on the outer surface 72 of the ear flaps 54 are properly oriented to engage with the third fastening element 45 disposed on the garment surface 49 of the chassis 46 in the front waist region 34. However, if the third fastening element 45 is disposed on the body facing surface 48 of the chassis 46, the first fastening elements 42 would be engaged with the third fastening element 45 in the folded configuration described above and the second fastening elements 44 would be engaged with the third fastening element 45 in traditional configurations. The waist feature 62 or any portion thereof may also be folded longitudinally inwardly more than once if necessary or desired. Further, any portion of the waist feature 62 or ear flaps 54 may be twisted or rotated or folded in order to present the fastening elements in any desired configuration. Thus, it is not as important which fasteners engage in which configuration as it is important that the fastening system 40 be capable of holding the diaper 20 about the wearer in any of the contemplated traditional or folded configurations.

The waist feature 62 of the present invention may be elastically extensible in one or more directions. In one embodiment, at least a portion of the waist feature 62 is extensible in the lateral direction so as to provide improved fit and containment characteristics throughout the time the diaper 20 is worn. In other embodiments, the waist feature 62 is extensible in the longitudinal direction to provide better fit for a larger number of wearer sizes. Extensibility may be provided by any means known in the art, including, but not limited to elastics, ring rolling, pleating, the use of extensible materials, and the like. One preferred method of providing materials with elastic like behavior is described in more detail in U.S. Pat. No. 5,518,801 entitled "Web Materials Exhibiting Elastic-Like Behavior" issued to Chappell, et al. on May 21, 1996.

In other embodiments, the waist feature 62 may include two or more panels which are capable of being positioned independently of each other. For example, the waist feature 62 may include a panel adjacent and laterally inwardly from each ear flap 54. The panels may be separated by a slit, cut, perforation, or the like such that the all or a portion of the panels can be positioned independent all or a portion of the other panel(s). Thus, embodiments are contemplated wherein some panels are folded longitudinally inwardly over the body facing surface 48 of the chassis 46 and other panels are folded longitudinally inwardly over the garment facing surface 49 of the chassis 46 or not folded longitudinally inwardly. Each panel can have one or more holding members 86, as described below, to hold the panels in place once the desired configuration has been obtained.

Figure 10:
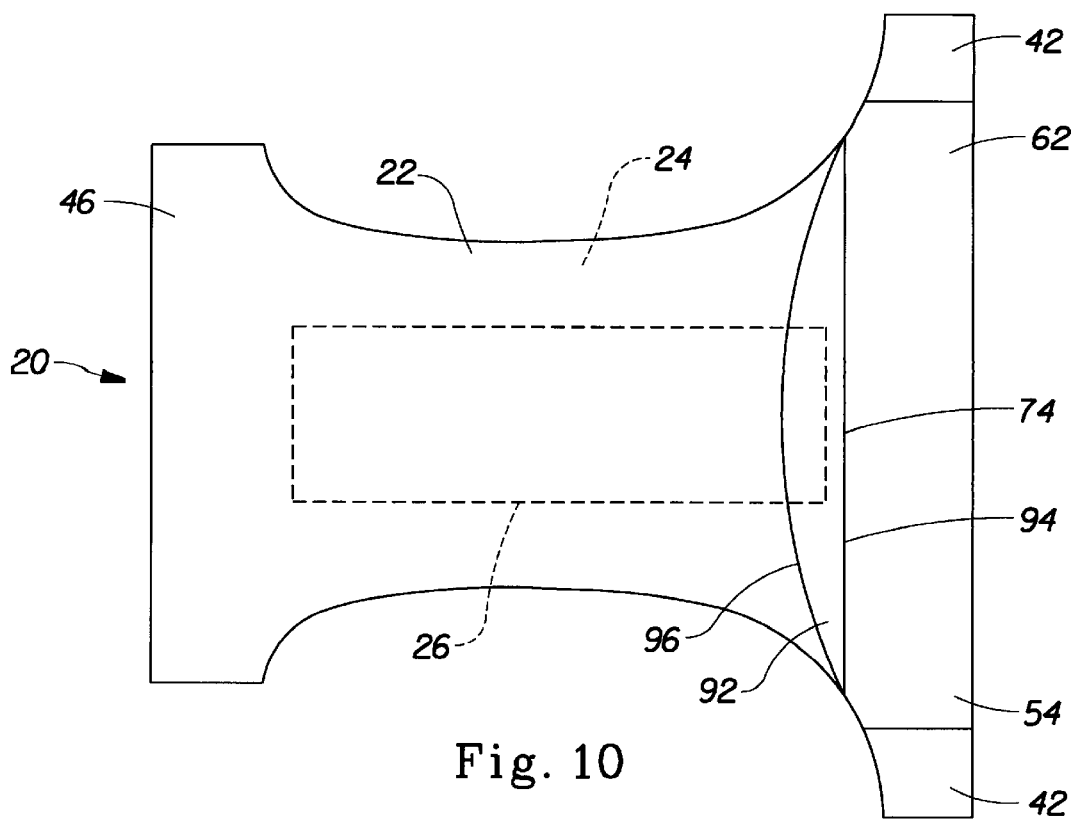
FIG. 10 is a plan view of an alternative embodiment of the disposable absorbent article of the present invention shown with the body facing side toward the viewer.
Figure 11:
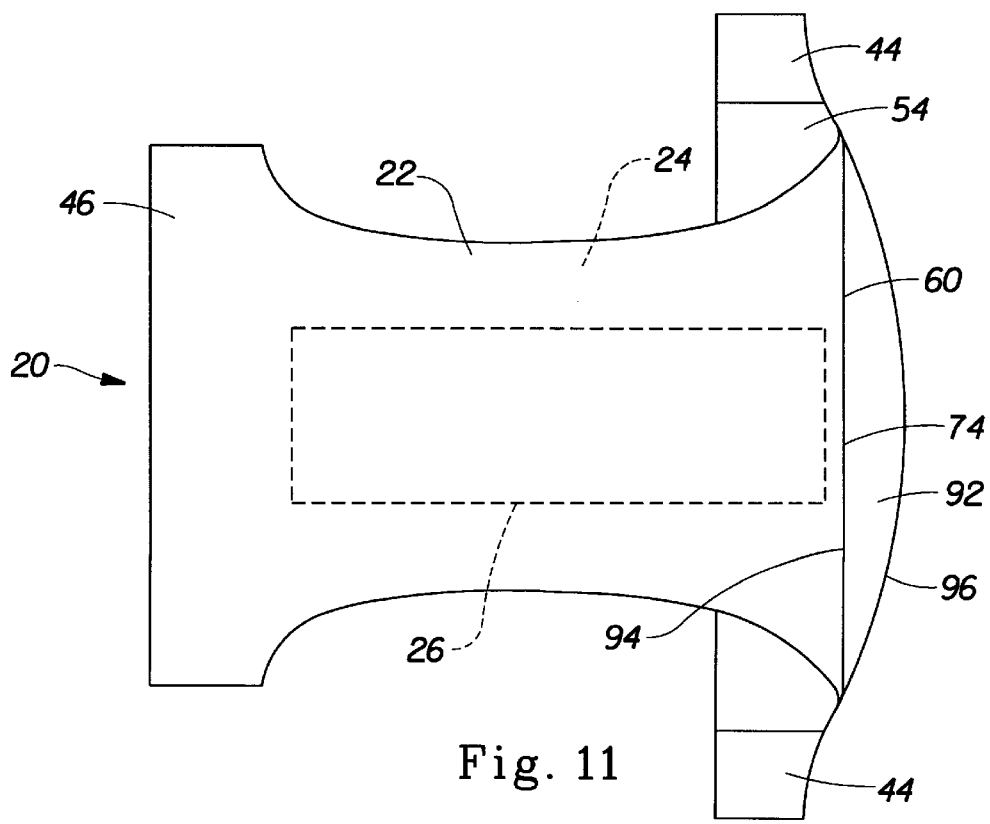
FIG. 11 is a plan view of an alternative embodiment of the disposable absorbent article of the present invention shown with the body facing side toward the viewer.

In another embodiment, the waist feature 62 may include one or more waist flaps 92 which can provide the article 20 with waist cap feature 90 or a finished edge, depending on the configuration of the diaper 20 when in use. As shown in FIG. 10, the diaper 20 has a waist feature 62 includes a waist flap 92 which is disposed in the rear waist region 38. Although it is preferred that the waist flap(s) 92 be disposed on the body facing surface 48 of the chassis 46 in the rear waist region 38, other embodiments are contemplated. The waist flap 92 has a proximal edge 94 and a distal edge 96. The waist flap proximal edge 94 is the portion of the waist flap 92 which is joined to the chassis 46. At least a portion of the waist flap distal edge 96 is unattached to the chassis 46. When the waist feature 62 is longitudinally extended, as shown in FIG. 10, the waist flap distal edge 96 is disposed longitudinally inwardly from the waist flap proximal edge 94. This provides the diaper 20 with a waist cap feature 90 which helps prevent exudates from escaping the diaper in the rear waist region 38. When the waist feature 62 is folded longitudinally inwardly over the body facing surface 48 of the chassis 46, as shown in FIG. 11, the waist flap distal edge 96 may be rotated about the fold 60 such that it is disposed longitudinally outwardly from the waist flap proximal edge 94. When disposed longitudinally outwardly, the waist flap 92 may provide more material for better containment in the rear waist region 38 or may provide the diaper 20 with a more finished look.

The waist flap 92 may be made of any known material suitable for use in a disposable absorbent article. Further, the waist flap 92 may be a separate member joined to the diaper 20 or may be integral with any other element or elements of the diaper 20. For example, the waist flap 92 may include the material of the topsheet 22, the backsheet 24 or both.

Figure 6:
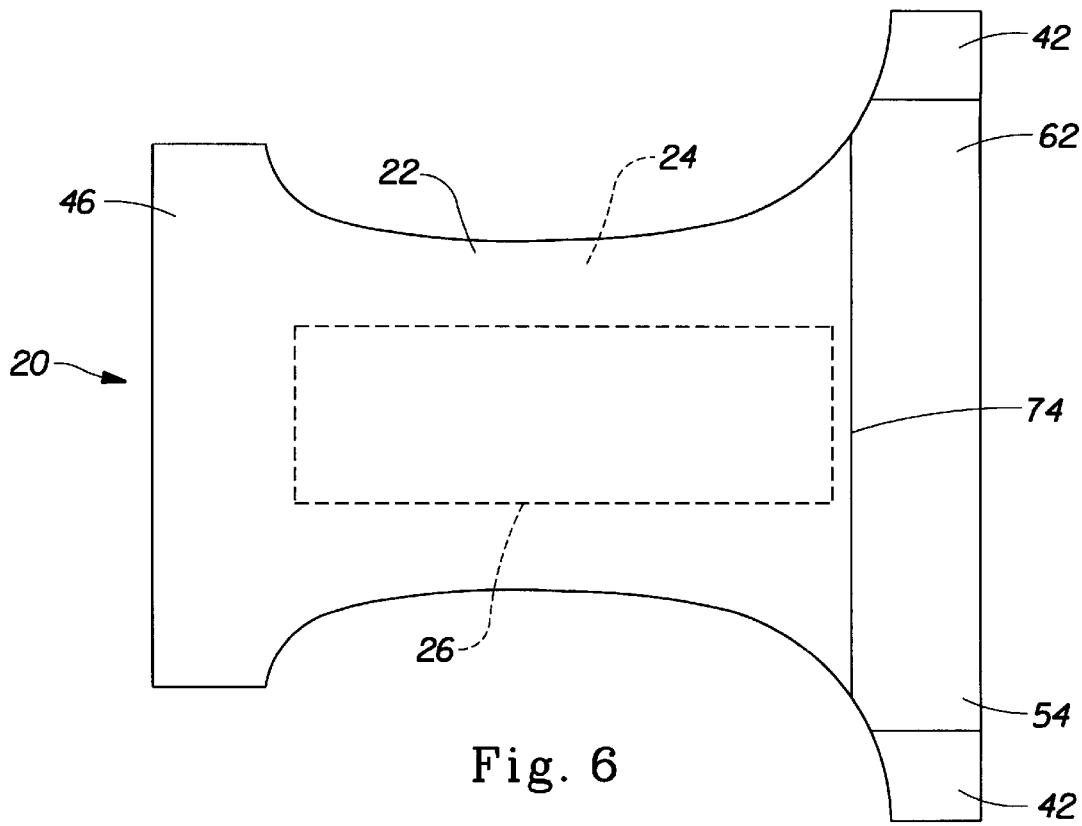
FIG. 6 is a plan view of an alternative embodiment of the disposable absorbent article of the present invention shown with the body facing side toward the viewer.
Figure 7:
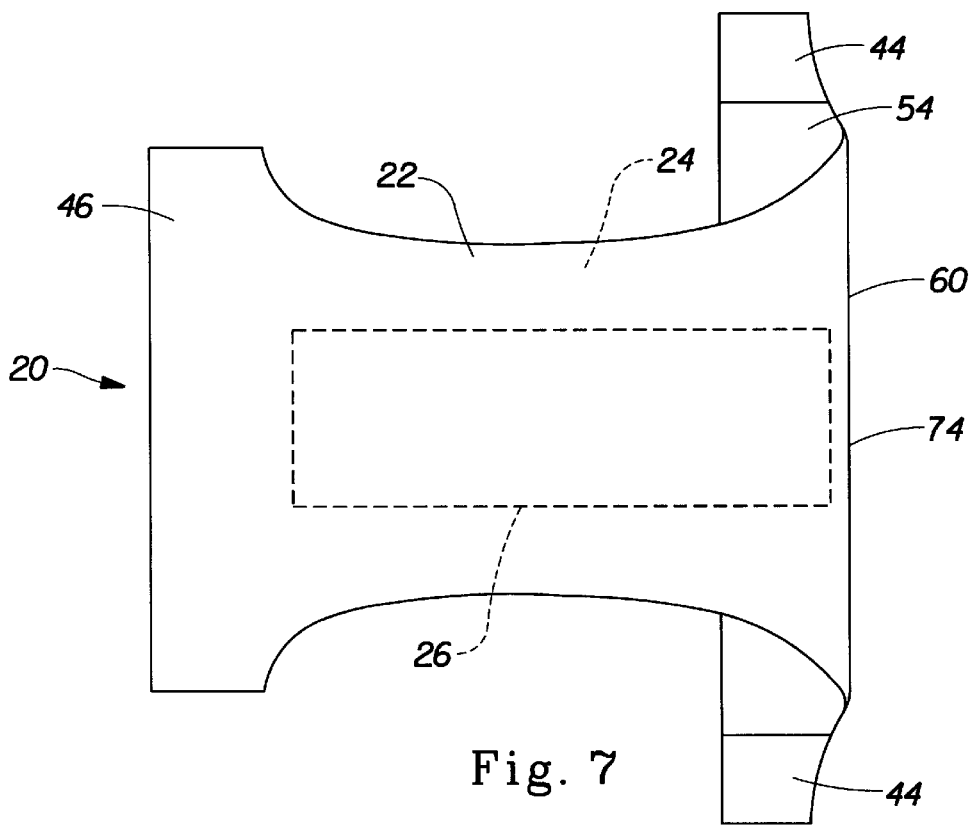
FIG. 7 is a plan view of an alternative embodiment of the disposable absorbent article of the present invention shown with the body facing side toward the viewer.
Figure 8:
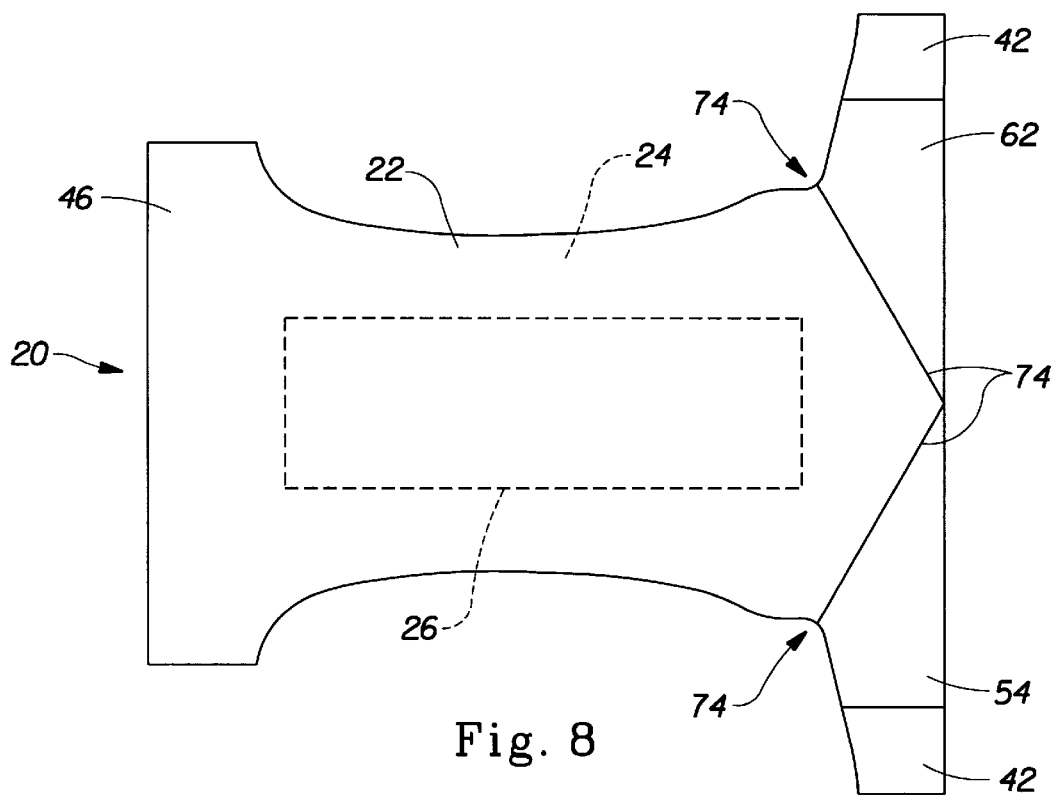
FIG. 8 is a plan view of an alternative embodiment of the disposable absorbent article of the present invention shown with the body facing side toward the viewer.
Figure 9:
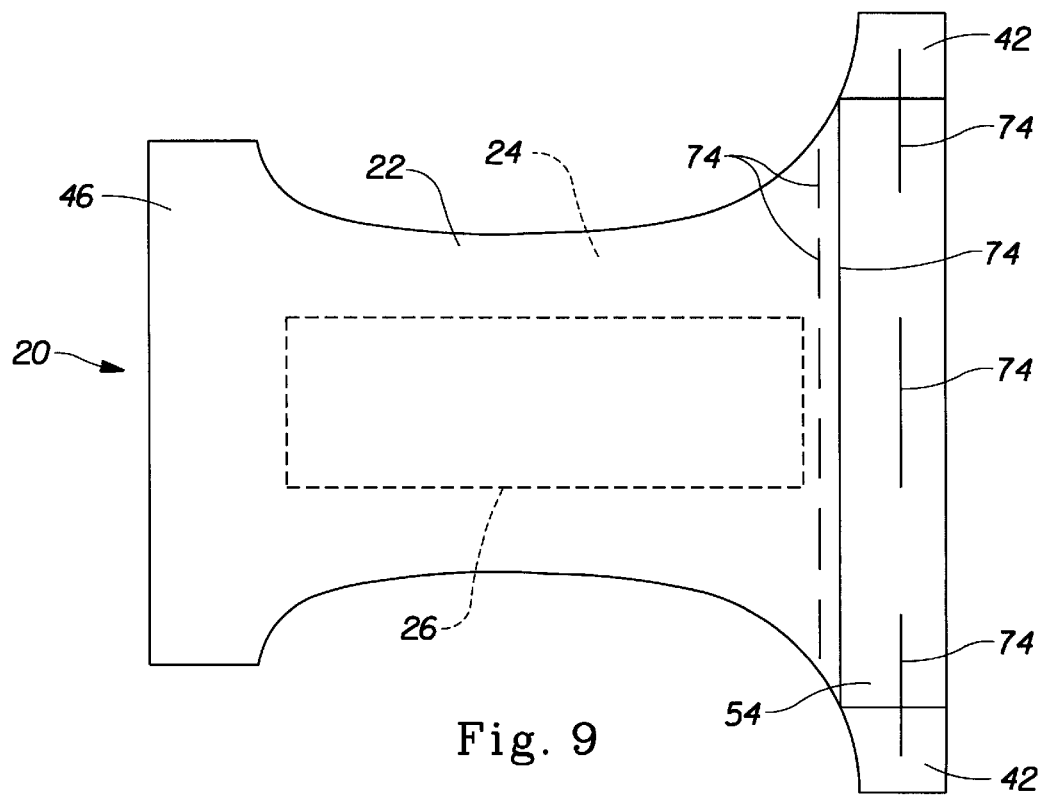
FIG. 9 is a plan view of an alternative embodiment of the disposable absorbent article of the present invention shown with the body facing side toward the viewer.

The diaper may also include one or more predetermined hinge points 74 or hinge lines. The predetermined hinge points 74 help the diaperer properly configure the rear waist region 38 of the diaper 20 when fitting it to a wearer. The predetermined hinge points 74 may be any means known in the art which aids the diaperer in folding the waist feature 62 about a specific "hinge" line. For example, the predetermined hinge point 74 may include a slit, perforation, weld, embossed region, cut out or crease. However, any other suitable means for providing the predetermined hinge point 74 may be used, including elastic strands and areas of low tensile strength. Further, the diaper 20 may include more than one predetermined hinge point 74 and more than one means for providing the hinge point 74. FIG. 6 shows a diaper 20 with a single predetermined hinge point 74. FIG. 7 is the same diaper as shown in FIG. 6, but with the waist feature 62 folded longitudinally inwardly about the predetermined hinge point 74. FIG. 8 shows an example of a predetermined hinge point 74 provided by a pair of cut out regions in the chassis 46. FIG. 9 shows a diaper 20 with multiple predetermined hinge points 74, one of which is located through at least a portion of the fastening system 40. Other embodiments of the present invention include hinge points 74 extending parallel to the longitudinal centerline 100 or at an angle to the lateral centerline 110 and the longitudinal centerline 100.

Embodiments of the present invention may also include a means for holding the waist feature 62 in the longitudinally inwardly folded configurations. The holding means 84 may include any known means for holding materials in an overlapping configuration. For example, the holding means 82 may include one or more holding members 86 such as the tape or hook and loop fasteners described herein, snaps, buttons, cohesive materials, zippers, pins, or any combination of these or any other known fastening or holding means. Further, the holding means 84 may include regions of static electricity or magnetic field(s), and the like.

The holding means 84 may be provided to hold the waist feature 62 in any folded configuration. Thus, the holding means 84 may be disposed on the garment facing surface 49 of the chassis 46 in the rear waist region 38 or the crotch region 36 and/or may be disposed on any portion of the waist feature 62. The holding means 84 may also be disposed on the body facing surface 48 of the chassis 46 in the rear waist region 38 or the crotch region 36 of the diaper 20. In any case, the holding means 84 should be provided such that it does not irritate the skin of the wearer reduce the effectiveness of the diaper or damage the wearer's clothing or bedding.

Figure 12:
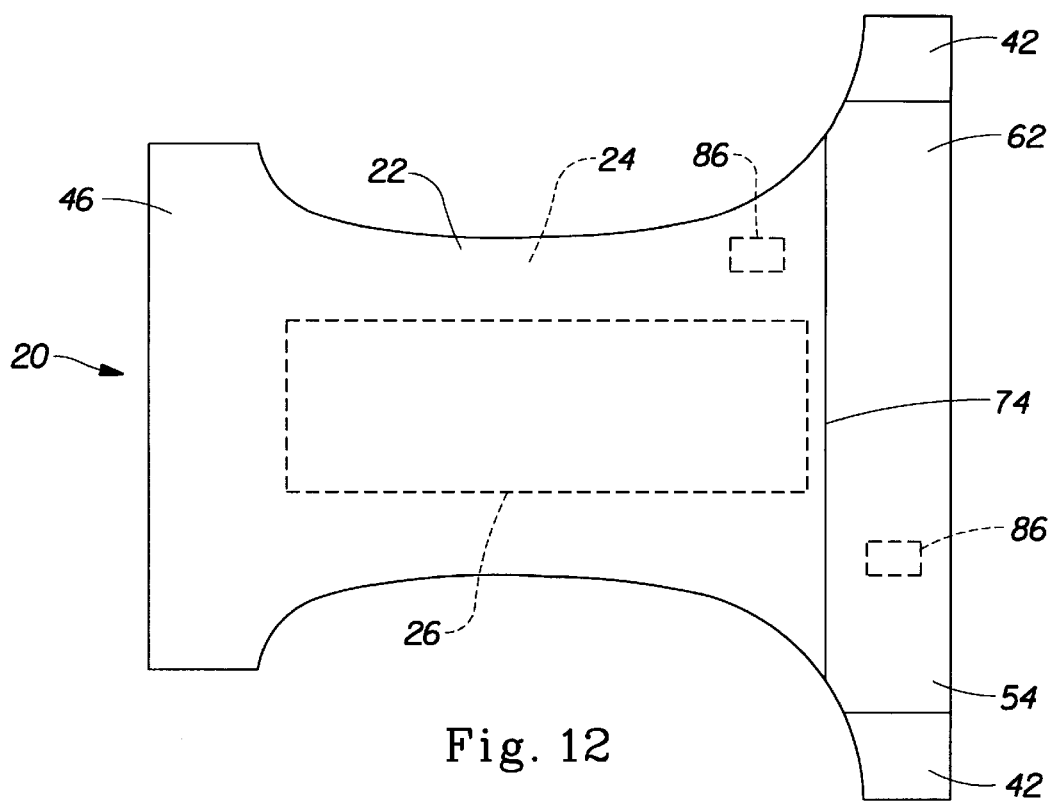
FIG. 12 is a plan view of an alternative embodiment of the disposable absorbent article of the present invention shown with the body facing side toward the viewer.
Figure 13:
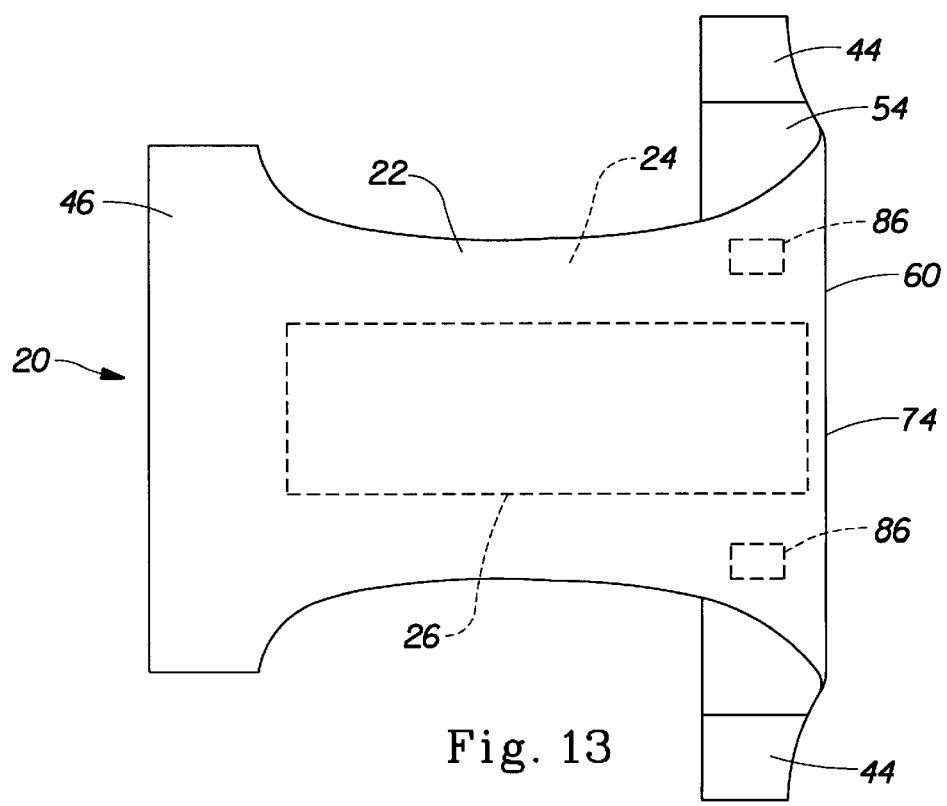
FIG. 13 is a plan view of an alternative embodiment of the disposable absorbent article of the present invention shown with the body facing side toward the viewer.

In another embodiment, the present invention may include a fold up waist feature 62 as shown in FIGS. 12 and 13. The fold up waist feature 62 may be similar to the waist feature 62 described above. However, the diaper 20 is provided with at least a portion of the fold up waist feature 62 folded over and releasably joined to the chassis 46. This allows the diaperer to increase the longitudinal length of the diaper by folding up or extending longitudinally the waist feature 62. The portion of the fold up waist feature 62 which is folded over the chassis 46 may be joined thereto by one or more holding member(s) 86. The holding member(s) 86 may be disposed on the chassis 46, the waist feature 62 or both.

The diaper 20 of the present invention may be fitted to the wearer by first placing the rear waist region of the diaper 20 in its flat-out configuration under the back of the wearer. The front waist region 34 is then pulled between the wearer's legs and toward the front waist of the wearer. The diaper 20 may then be adjusted in length by folding the waist feature 62 longitudinally inwardly. (If the waist feature 62 is folded for use, it may be folded before or after the diaper 20 is placed under the wearer.) The waist feature 62 may be folded either over the body facing surface 48 of the chassis 46 to form a waist cap 90 in the rear waist region of the diaper 20 or may be folded over the garment facing surface 49 of the chassis 46. In any case, the diaper is then fastened about the wearer by means of the fastening system 40. If the waist feature 62 has not been folded longitudinally inwardly, the first fastening element(s) 42 may be engaged with the third fastening element(s) 45 to join the ear flaps 54 of the rear waist region 38 with the front waist region 34 forming leg and waist closures. If the waist feature 62 has been folded longitudinally inwardly, the second fastening element(s) 44 may be engaged with the third fastening element(s) 45 to join the ear flaps 54 of the rear waist region 38 with the front waist region 34 forming leg and waist closures. (Of course, other fastening configurations are contemplated such as when the third fastening element 45 is disposed on the body facing surface 48 of the chassis.) Alternatively, the diaper 20 may be constructed as described above prior to application to the wearer such that it may be pulled on.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region, a rear waist region, a crotch region located between the front waist region and the rear waist region, a longitudinal centerline and a lateral centerline; the disposable absorbent article including:

a chassis, having a body facing surface and a garment facing surface, the chassis comprising a topsheet forming at least a portion of the body facing surface of the chassis, a backsheet joined with the topsheet the backsheet forming at least a portion of the garment facing surface of the chassis, and a core disposed between the topsheet and the backsheet, the core having a front waist edge, a rear waist edge and a pair of longitudinal edges;

a fold down waist feature disposed in the rear waist region, the fold down waist feature extending longitudinally outwardly from the rear waist edge of the core and including at least one ear flap extending laterally outwardly beyond one of the longitudinal edges of the core, the ear flap having an inner surface and an opposed outer surface; the fold down waist feature further including a waist flap having a waist flap proximal edge and a waist flap distal edge, the waist flap proximal edge being joined with the chassis in the rear waist region and at least a portion of the waist flap distal edge being unsecured to the chassis such that when the fold down waist feature is folded longitudinally inwardly at least a portion of the waist flap distal edge may be disposed longitudinally outwardly from the waist flap proximal edge.

2. The disposable absorbent article of claim 1 further including a fastening system for joining a portion of the front waist region and a portion of the rear waist region, the fastening system including a first fastening element disposed on the inner surface of the side panel, a second fastening element disposed on the outer surface of the side panel and a third fastening element disposed on the garment facing surface of the chassis in the front waist region, both the first fastening element and the second fastening element being separately engageable with the third fastening element such that the absorbent article may be fitted to a wearer in a first configuration wherein the first fastening element is engaged with the third fastening element and a second configuration wherein at least a portion of the waist feature is folded longitudinally inwardly and the second fastening element is engaged with the third fastening element.

3. A disposable absorbent article having a front waist region, a rear waist region, a crotch region located between the front waist region and the rear waist region, a longitudinal centerline and a lateral centerline; the disposable absorbent article including:

a chassis, having a body facing surface and a garment facing surface, the chassis comprising a topsheet forming at least a portion of the body facing surface of the chassis, a backsheet joined with the topsheet the backsheet forming at least a portion of the garment facing surface of the chassis, and a core disposed between the topsheet and the backsheet, the core having a front waist edge, a rear waist edge and a pair of longitudinal edges;

a fold down waist feature disposed in the rear waist region, the fold down waist feature extending longitudinally outwardly from the rear waist edge of the core and including at least one ear flap extending laterally outwardly beyond one of the longitudinal edges of the core, the ear flap having an inner surface and an opposed outer surface; the fold down waist feature further including a waist flap having a waist flap proximal edge and a waist flap distal edge, the waist flap proximal edge being joined with the chassis in the rear waist region and at least a portion of the waist flap distal edge being unsecured to the chassis such that when the fold down waist feature is in a longitudinally extended configuration the waist flap proximal edge is disposed longitudinally outwardly from the waist flap distal edge and when the fold down waist feature is folded longitudinally inwardly the waist flap proximal edge is disposed longitudinally inwardly from the waist flap distal edge.

4. A disposable absorbent article having a front waist region, a rear waist region, a crotch region located between the front waist region and the rear waist region, a longitudinal centerline and a lateral centerline; the disposable absorbent article including:

a chassis, having a body facing surface and a garment facing surface, the chassis comprising a topsheet forming at least a portion of the body facing surface of the chassis, a backsheet joined with the topsheet the backsheet forming at least a portion of the garment facing surface of the chassis, and a core disposed between the topsheet and the backsheet, the core having a front waist edge, a rear waist edge and a pair of longitudinal edges;

a fold down waist feature disposed in the rear waist region, the fold down waist feature extending longitudinally outwardly from the rear waist edge of the core and including at least one ear flap extending laterally outwardly beyond one of the longitudinal edges of the core, the ear flap having an inner surface and an opposed outer surface; the fold down waist feature further including a waist flap having a waist flap proximal edge and a waist flap distal edge, and longitudinal sides, the waist flap longitudinal sides being substantially unattached to the fold down waist feature, the waist flap proximal edge being joined with the chassis in the rear waist region and at least a portion of the waist flap distal edge being unsecured to the chassis such that when the fold down waist feature is folded longitudinally inwardly at least a portion of the waist flap distal edge may be disposed longitudinally outwardly from the waist flap proximal edge or longitudinally inwardly from the waist flap proximal edge.

* * * * *